(12) United States Patent
Ding et al.

(10) Patent No.: US 7,856,270 B2
(45) Date of Patent: *Dec. 21, 2010

(54) CARDIAC PACING USING ADJUSTABLE ATRIO-VENTRICULAR DELAYS

(75) Inventors: Jiang Ding, Shoreview, MN (US); Yinghong Yu, Maplewood, MN (US); Andrew P. Kramer, Minneapolis, MN (US); Julio Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1102 days.

This patent is subject to a terminal disclaimer.

(21) Appl. No.: 11/049,181

(22) Filed: Feb. 2, 2005

(65) Prior Publication Data

US 2005/0131472 A1 Jun. 16, 2005

Related U.S. Application Data

(63) Continuation of application No. 10/615,202, filed on Jul. 7, 2003, now Pat. No. 6,859,665, which is a continuation of application No. 10/243,811, filed on Sep. 13, 2002, now Pat. No. 6,684,103, which is a continuation of application No. 10/008,830, filed on Dec. 7, 2001, now Pat. No. 6,542,775, which is a continuation of application No. 09/661,608, filed on Sep. 14, 2000, now Pat. No. 6,351,673, which is a continuation of application No. 09/492,911, filed on Jan. 20, 2000, now Pat. No. 6,360,127, which is a continuation of application No. 09/075,278, filed on May 8, 1998, now Pat. No. 6,144,880.

(51) Int. Cl.
*A61N 1/365* (2006.01)

(52) U.S. Cl. ...................................................... 607/25

(58) Field of Classification Search ..................... 607/9, 607/17, 23–25, 27
See application file for complete search history.

(56) References Cited

U.S. PATENT DOCUMENTS 4,401,119 A 8/1983 Herpers (Continued)

FOREIGN PATENT DOCUMENTS

EP 0474958 3/1992

(Continued)

OTHER PUBLICATIONS

Ding, J., et al., "Method and Apparatus for Setting Pacing Parameters in Cardiac Resynchronization Therapy", U.S. Appl. No. 10/352,780, filed Jan. 28, 2003, 34 pages.

(Continued)

*Primary Examiner*—George R Evanisko
(74) *Attorney, Agent, or Firm*—Scwhegman, Lundberg & Woessner, P.A.

(57) ABSTRACT

A pacing system for providing optimal hemodynamic cardiac function for parameters such as contractility (peak left ventricle pressure change during systole or LV+dp/dt), or stroke volume (aortic pulse pressure) using system for calculating atrio-ventricular delays for optimal timing of a ventricular pacing pulse. The system providing an option for near optimal pacing of multiple hemodynamic parameters. The system deriving the proper timing using electrical or mechanical events having a predictable relationship with an optimal ventricular pacing timing signal.

20 Claims, 7 Drawing Sheets

U.S. PATENT DOCUMENTS

| | | | |
|---|---|---|---|
| 4,432,362 | A | 2/1984 | Leckrone et al. |
| 4,922,907 | A | 5/1990 | Hedin et al. |
| 4,928,688 | A | 5/1990 | Mower |
| 5,101,824 | A | 4/1992 | Lekholm |
| 5,139,020 | A | 8/1992 | Koestner et al. |
| 5,161,540 | A | 11/1992 | Mueller |
| 5,168,869 | A | 12/1992 | Chirife |
| 5,179,949 | A | 1/1993 | Chirife |
| 5,318,595 | A | 6/1994 | Ferek-Petric et al. |
| 5,330,511 | A | 7/1994 | Boute |
| 5,334,222 | A | 8/1994 | Salo et al. |
| 5,372,607 | A | 12/1994 | Stone et al. |
| 5,514,163 | A | 5/1996 | Markowitz et al. |
| 5,527,347 | A | 6/1996 | Shelton et al. |
| 5,549,650 | A | 8/1996 | Bornzin et al. |
| 5,554,177 | A | 9/1996 | Kieval et al. |
| 5,609,612 | A | 3/1997 | Plicchi et al. |
| 5,626,620 | A | 5/1997 | Kieval et al. |
| 5,626,623 | A | 5/1997 | Kieval et al. |
| 5,628,777 | A | 5/1997 | Moberg et al. |
| 5,690,689 | A | 11/1997 | Sholder |
| 5,700,283 | A | 12/1997 | Salo |
| 5,713,930 | A | 2/1998 | van der Veen et al. |
| 5,716,383 | A | 2/1998 | Kieval et al. |
| 5,749,906 | A | 5/1998 | Kieval et al. |
| 5,800,471 | A | 9/1998 | Baumann |
| 6,144,880 | A * | 11/2000 | Ding et al. ............ 607/23 |
| 6,208,901 | B1 | 3/2001 | Hartung |
| 6,223,082 | B1 | 4/2001 | Bakels et al. |
| 6,280,389 | B1 | 8/2001 | Ding et al. |
| 6,304,777 | B1 | 10/2001 | Ben-Haim et al. |
| 6,311,089 | B1 | 10/2001 | Mann et al. |
| 6,351,673 | B1 * | 2/2002 | Ding et al. ............ 607/24 |
| 6,360,127 | B1 | 3/2002 | Ding et al. |
| 6,430,439 | B1 | 8/2002 | Wentkowski et al. |
| 6,438,421 | B1 | 8/2002 | Stahmann et al. |
| 6,449,510 | B1 | 9/2002 | Albers et al. |
| 6,480,742 | B2 | 11/2002 | Stahmann et al. |
| 6,507,756 | B1 | 1/2003 | Heynen et al. |
| 6,512,952 | B2 | 1/2003 | Stahmann et al. |
| 6,522,921 | B2 | 2/2003 | Stahmann et al. |
| 6,522,923 | B1 | 2/2003 | Turcott |
| 6,542,775 | B2 * | 4/2003 | Ding et al. ............ 607/24 |
| 6,553,258 | B2 | 4/2003 | Stahmann et al. |
| 6,597,951 | B2 | 7/2003 | Kramer et al. |
| 6,684,103 | B2 * | 1/2004 | Ding et al. ............ 607/23 |
| 6,856,836 | B2 * | 2/2005 | Ding et al. ............ 607/17 |
| 7,110,817 | B2 * | 9/2006 | Yu et al. ............ 607/23 |
| 7,529,585 | B2 * | 5/2009 | Yu et al. ............ 607/9 |
| 2001/0047194 | A1 | 11/2001 | Thompson et al. |
| 2002/0123769 | A1 | 9/2002 | Panken et al. |
| 2002/0183795 | A1 | 12/2002 | Rouw et al. |
| 2003/0097158 | A1 | 5/2003 | Belalcazar |
| 2003/0105496 | A1 | 6/2003 | Yu et al. |
| 2003/0144702 | A1 | 7/2003 | Yu et al. |
| 2003/0144703 | A1 | 7/2003 | Yu et al. |
| 2004/0019365 | A1 | 1/2004 | Ding et al. |
| 2004/0078059 | A1 | 4/2004 | Ding et al. |
| 2009/0198299 | A1 | 8/2009 | Yu et al. |

FOREIGN PATENT DOCUMENTS

| | | | |
|---|---|---|---|
| EP | 0970721 | A2 | 1/2000 |

OTHER PUBLICATIONS

Kramer, Andrew P., et al., "Automatic Selection From Multiple Cardiac Optimization Protocols", U.S. Appl. No. 10/624,458, filed Jul. 21, 2003, 49 pages.

Ritter, P., et al., "A Built-In System Based on the Peak Endocardial Acceleration (PEA) for AV-Delay Optimization in DDDR Pacing", PACE, 20(5)(Part II), (Abstract of Paper presented at EUROPACE '97),(May 1997),p. 1567.

"U.S. Appl. No. 10/314,899 Final Office Action mailed Apr. 24, 2006", 11 pgs.

"U.S. Appl. No. 10/314,899 Non Final Office Action mailed Dec. 15, 2005", 17 pgs.

"U.S. Appl. No. 10/314,899 Response filed Mar. 15, 2006 to Non Final Office Action mailed Dec. 15, 2005", 11 pgs.

"U.S. Appl. No. 10/314,899 Response filed Jun. 23, 2006 to Final Office Action mailed Apr. 24, 2006", 10 pgs.

"U.S. Appl. No. 10/314,910 Non Final Office Action mailed Dec. 16, 2005", 19 pgs.

"U.S. Appl. No. 10/314,910 Response filed Mar. 16, 2006 to Non Final Office Action mailed Dec. 16, 2005", 14 pgs.

"PCT Application No. PCT/US2004/002332 International Search Report mailed Jan. 28, 2004", 7 pgs.

"PCT Application No. PCT/US2004/002332 Written Opinion mailed Jan. 28, 2004", 7 pgs.

"U.S. Appl. No. 09/075,278, Advisory Action mailed Jan. 28, 2000", 2 pgs.

"U.S. Appl. No. 09/075,278, Advisory Action mailed Dec. 2, 1999", 1 pg.

"U.S. Appl. No. 09/075,278, Amendment Under 37 CFR Sec. 1.116 filed Jan. 28, 2000", 2 pgs.

"U.S. Appl. No. 09/075,278, Amendment Under 37 CFR Sec. 1.116 filed Feb. 11, 2000", 7 pgs.

"U.S. Appl. No. 09/075,278, Final Office Action mailed Sep. 17, 1999", 9 pgs.

"U.S. Appl. No. 09/075,278, Non-Final Office Action mailed Apr. 12, 1999", 10 pgs.

"U.S. Appl. No. 09/075,278, Notice of Allowance mailed Feb. 14, 2000", 4 pgs.

"U.S. Appl. No. 09/075,278, Preliminary Amendment filed Nov. 16, 1998", 8 pgs.

"U.S. Appl. No. 09/075,278, Response filed Aug. 12, 1999 to Non-Final Office Action mailed Apr. 12, 1999", 16 pgs.

"U.S. Appl. No. 09/075,278, Response filed Nov. 17, 1999 to Final Office Action mailed Sep. 17, 1999", 4 pgs.

"U.S. Appl. No. 09/075,278, Response filed Dec. 17, 1999 to Final Office Action mailed Sep. 17, 1999 and Advisory Action mailed Dec. 2, 1999", 4 pgs.

"U.S. Appl. No. 09/492,911, Amendment Under 37 C.F.R. Sec. 1.312(a) filed Oct. 16, 2001", 3 pgs.

"U.S. Appl. No. 09/492,911, Non-Final Office Action mailed Oct. 27, 2000", 6 pgs.

"U.S. Appl. No. 09/492,911, Notice of Allowance Mar. 20, 2001", 8 pgs.

"U.S. Appl. No. 09/492,911, Notice of Allowance mailed Jul. 16, 2001", 3 pgs.

"U.S. Appl. No. 09/492,911, Preliminary Amendment filed Jan. 20, 2000", 4 pgs.

"U.S. Appl. No. 09/492,911, Response filed Jan. 29, 2001 to Non-Final Office Action mailed Oct. 27, 2000", 7 pgs.

"U.S. Appl. No. 09/492,911, Response filed Sep. 14, 2000 to Restriction Requirement mailed Aug. 15, 2000", 4 pgs.

"U.S. Appl. No. 09/492,911, Restriction Requirement mailed Aug. 15, 2000", 4 pgs.

"U.S. Appl. No. 09/661,608, Non-Final Office Action mailed Feb. 28, 2001", 6 pgs.

"U.S. Appl. No. 09/661,608, Notice of Allowance mailed Aug. 27, 2001", 3 pgs.

"U.S. Appl. No. 09/661,608, Preliminary Amendment filed Sep. 14, 2000", 4 pgs.

"U.S. Appl. No. 09/661,608, Response filed Jun. 28, 2001 to Non-Final Office Action mailed Feb. 28, 2001", 11 pgs.

"U.S. Appl. No. 09/661,608, Supplement Amendment filed Aug. 24, 2001", 4 pgs.

"U.S. Appl. No. 09/661,608, Supplemental Notice of Allowance mailed Oct. 18, 2001", 2 pgs.

"U.S. Appl. No. 10/008,830, Non-Final Office Action mailed May 23, 2002", 10 pgs.

"U.S. Appl. No. 10/008,830, Notice of Allowance mailed Oct. 30, 2002", 8 pgs.

"U.S. Appl. No. 10/008,830, Preliminary Amendment filed Dec. 7, 2001", 2 pgs.

"U.S. Appl. No. 10/008,830, Response filed Aug. 23, 2002 to Non-Final Office Action mailed May 23, 2002", 13 pgs.

"U.S. Appl. No. 10/008,830, Supplemental Preliminary Amendment filed Feb. 7, 2002", 4 pgs.

"U.S. Appl. No. 10/243,811, Non-Final Office Action mailed Mar. 20, 2003", 5 pgs.

"U.S. Appl. No. 10/243,811, Notice of Allowance mailed Sep. 3, 2003", 5 pgs.

"U.S. Appl. No. 10/243,811, Response filed Feb. 14, 2003 to Restriction Requirement mailed Jan. 14, 2003", 1 pg.

"U.S. Appl. No. 10/243,811, Response filed Jun. 16, 2003 to Non-Final Office Action mailed Mar. 20, 2003", 10 pgs.

"U.S. Appl. No. 10/243,811, Restriction Requirement mailed Jan. 14, 2003", 4 pgs.

"U.S. Appl. No. 10/314,899, Advisory Action mailed Jul. 11, 2006", 3 pgs.

"U.S. Appl. No. 10/314,899, Notice of Allowance mailed Aug. 23, 2006", 6 pgs.

"U.S. Appl. No. 10/314,910, Notice of Allowance mailed May 5, 2006", 8 pgs.

"U.S. Appl. No. 10/615,201, Non-Final Office Action mailed Jun. 3, 2004", 6 pgs.

"U.S. Appl. No. 10/615,201, Notice of Allowance mailed Oct. 4, 2004", 7 pgs.

"U.S. Appl. No. 10/615,201, Response filed Aug. 31, 2004 to Non-Final Office Action mailed Jun. 3, 2004", 9 pgs.

"U.S. Appl. No. 10/615,202, Non-Final Office Action mailed Jun. 14, 2004", 4 pgs.

"U.S. Appl. No. 10/615,202, Notice of Allowance mailed Oct. 4, 2004", 7 pgs.

"U.S. Appl. No. 10/615,202, Response filed Aug. 31, 2004 to Non-Final Office Action mailed Jun. 14, 2004", 9 pgs.

"U.S. Appl. No. 10/735,267, Notice of Allowance mailed Jun. 9, 2006", 6 pgs.

"U.S. Appl. No. 11/463,176, Non-Final Office Action mailed Aug. 14, 2008", 6 pgs.

"U.S. Appl. No. 11/463,176, Notice of Allowance mailed Dec. 24, 2008", 4 pgs.

"U.S. Appl. No. 11/463,176, Response filed Nov. 14, 2008 to Non Final Office Action mailed Aug. 14, 2008", 11 pgs.

"U.S. Appl. No. 11/674,773, Final Office Action mailed May 19, 2010", 7 pages.

"U.S. Appl. No. 11/674,773, Non-Final Office Action mailed Oct. 21, 2009", 7 pgs.

"U.S. Appl. No. 11/674,773, Response filed Feb. 17, 2010 to Non Final Office Action mailed Oct. 21, 2009", 15 pgs.

"International Application Serial No. PCT/US99/10142, International Search Report mailed Aug. 23, 1999", 6 pgs.

* cited by examiner

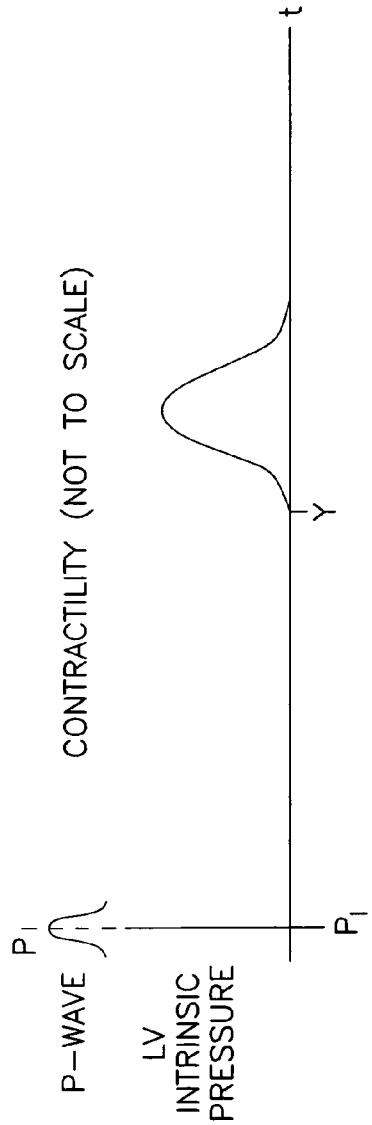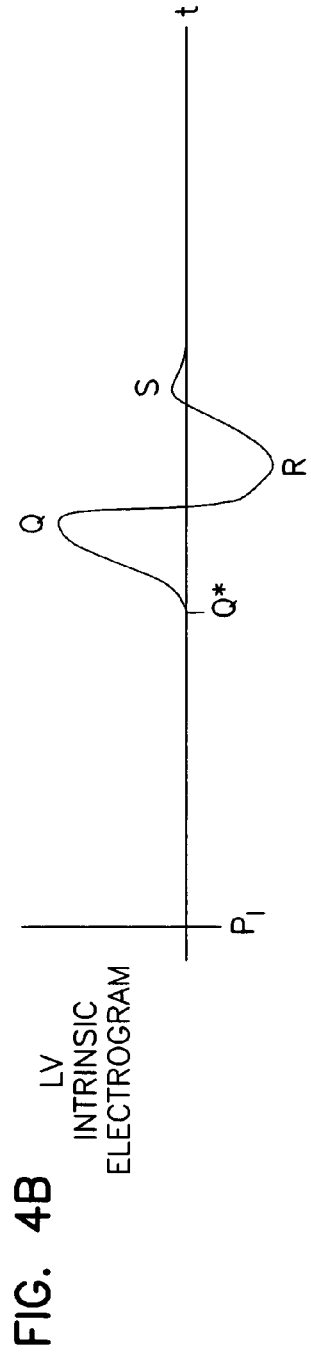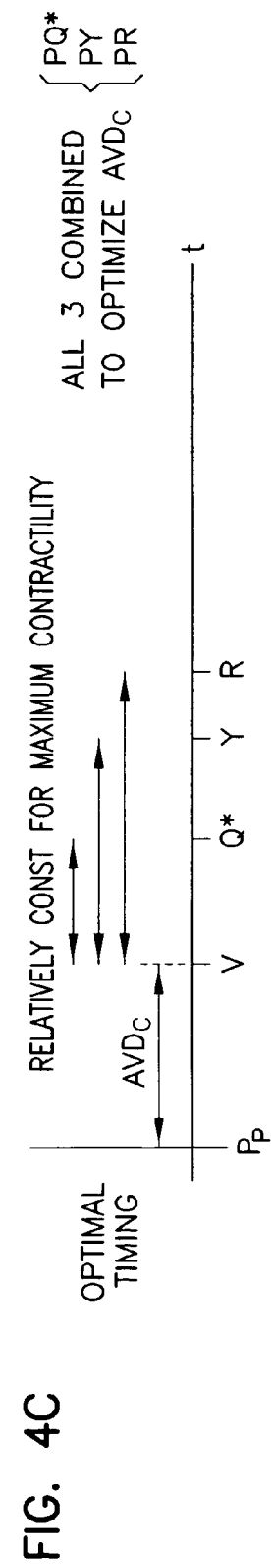
FIG. 4A
FIG. 4B
FIG. 4C

US 7,856,270 B2

CARDIAC PACING USING ADJUSTABLE ATRIO-VENTRICULAR DELAYS

CROSS REFERENCE TO RELATED APPLICATIONS

This application is a continuation of U.S. patent application Ser. No. 10/615,202, filed on Jul. 7, 2003, now issued as U.S. Pat. No. 6,859,665, which is a continuation of U.S. patent application Ser. No. 10/243,811, filed on Sep. 13, 2002, now issued as U.S. Pat. No. 6,684,103, which is a continuation of U.S. patent application Ser. No. 10/008,830, filed on Dec. 7, 2001, now issued as U.S. Pat. No. 6,542,775, which is a continuation of U.S. patent application Ser. No. 09/661,608, filed on Sep. 14, 2000, now issued as U.S. Pat. No. 6,351,673, which is a continuation of U.S. patent application Ser. No. 09/492,911, filed on Jan. 20, 2000, now issued as U.S. Pat. No. 6,360,127, which is a continuation of U.S. patent application Ser. No. 09/075,278, filed May 8, 1998, now issued as U.S. Pat. No. 6,144,880, the specifications of which are incorporated herein by reference.

This application is related to co-pending, commonly assigned U.S. patent application Ser. No. 10/615,201, entitled "CARDIAC PACING USING ADJUSTABLE ATRIO-VENTRICULAR DELAYS," filed on Jul. 7, 2003, now issued as U.S. Pat. No. 6,856,836, which is hereby incorporated by reference in its entirety.

FIELD OF THE INVENTION

The present invention relates generally to a method and apparatus for cardiac pacing and, in particular, to a pacing system providing adjustable atrio-ventricular time delays to improve different heart performance parameters.

BACKGROUND OF THE INVENTION

The heart is the center of the circulatory system. It is an organ which performs two major pumping functions and may be divided into right and left heart "pumps." The left heart pump draws oxygenated blood from the lungs and pumps it to the organs of the body. The right heart pump draws blood from the body organs and pumps it into the lungs. For a human heart, the right heart pump is on a patient's right side and the left heart pump is on the patient's left side. Figures in this document, such as FIG. 1, show a "top" view of the heart, which is the view that a physician observes during open heart surgery. Therefore, the left heart pump is on the right hand side of the FIG. 1 and the right heart pump is on the left hand side of FIG. 1. Each heart pump includes an upper chamber called an atrium and a lower chamber called a ventricle. The left heart pump therefore contains a left atrium (LA) and a left ventricle (LV), separated by a valve called the mitral valve. The right heart pump contains a right atrium (RA) and a right ventricle (RV), separated by a valve called the tricuspid valve.

The blood flows in the circulatory system in the following path: from the peripheral venous system (blood which has transferred through the body organs) to the RA, from the RA to the RV through the tricuspid valve, from RV to the pulmonary artery through the pulmonary valve, to the lungs. Oxygenated blood from the lungs is drawn from the pulmonary vein to the LA, from the LA to the LV through the mitral valve, and finally, from the LV to the peripheral arterial system (transferring blood to the organs of the body) through the aortic valve.

Normally, the heart pumps operate in synchrony and ensure the proper pumping action to provide oxygenated blood from the lungs to the organs of the body. A normal heart provides this synchrony by a complex conduction system which propagates electrical pulses to the heart muscle tissue to perform the necessary atrial and ventricular contractions. A heartbeat is the result of a regular train of electrical pulses to the proper portions of the heart to provide rhythmic heart pumping. The heart muscle provides pumping by the contraction of muscle tissue upon receipt of an electrical signal, and the pumping action is made possible through a system of heart valves which enable blood flow in a single direction. Thus, the heart includes a complex electrical and mechanical network.

To pump blood through the circulatory system, a beating heart performs a cardiac cycle. A cardiac cycle consists of a systolic phase and a diastolic phase. During systole, the ventricular muscle cells contract to pump blood through both the pulmonary circulation and the systemic circulation. During diastole, the ventricular muscle cells relax, which causes pressure in the ventricles to fall below that in the atria, and the ventricles begin to be refilled with blood.

In normal condition, the cardiac pumping is highly efficient. One aspect of this high efficiency is due to sequential atrio-ventricular contraction. Near the end of diastole, the atria contract, causing an extra amount of blood to be forced into the ventricles. Thus, the ventricles have more blood (preload) to pump out during next systole. Another aspect of this high efficiency in blood pumping is contributed from a network or fast ventricular conduction system. As shown in FIG. 1, the system includes right and left bundle branches of conductive tissues that extend from the Bundle of His and the massive network of fast conducting Purkinje fibers that cover most of the endocardial surface of the ventricles. Electrical signals coming from the atrium are relayed to the Purkinje fibers through the bundle branches, and to the different regions of the ventricles by the Purkinje fiber network. Therefore the entire ventricular muscle cells can contract synchronously during systole. This synchronized contraction enhances the strength of the pumping power.

To assess the cardiac function, it is important to examine the LV systolic performance which directly determines the ability of the heart to pump blood through the systemic circulation. There are multiple ways to assess the performance of the heart. One way is to examine how well the LV contracts in order to determine the effectiveness of the LV as a pump. As can be seen from FIG. 2, the LV starts to contract after an electrical signal propagating down the left bundle branches stimulates muscle cells of septal wall M and lateral wall N. In FIG. 3, the walls M and N are contracting such that they are forced towards each other to pump blood out of the ventricle. One measure of LV contraction effectiveness is called "contractility." Left ventricular contractility is a measure of overall strength of the contracting power of the LV muscle cells. It is a function of the health of the LV muscle tissue and the coordination of the contractions of the entire LV, including walls M and N. Such coordination depends on the health of the left bundle branches and on the health of the fast conducting Purkinje fiber network. LV contractility is estimated by measuring the peak positive rate of change of the LV pressure during systole. In mathematical terms, this is the maximum positive derivative of the LV pressure, which is denoted by the term "LV+dp/dt".

LV systolic performance is also measured by stroke volume, which is the volume of blood pumped out of the LV per systole. Stroke volume can be estimated by measuring aortic pulse pressure (PP).

Cardiac muscle cells need to be electrically excited before they can have a mechanical contraction. During the excitation (depolarization), electrical signals will be generated and they can be recorded both intracardially and extracardially. The recorded signals are generally called electrocardiogram (ECG). An ECG recorded intracardially is also called an electrogram, which is recorded from an electrode placed endocardially or epicardially in an atrium or a ventricle. An ECG recorded extracardially is often called surface ECG, because it is usually recorded from two or more electrodes attached to the skin of the body. A complete surface ECG recording is from 12-lead configuration.

The features in ECG are labeled according to the origin of the electrical activity. The signals corresponding to intrinsic depolarization in an atrium and a ventricle are called P-wave and QRS complex, respectively. The QRS complex itself consists of a Q-wave, a R-wave, and a S-wave. The time interval from P-wave to R-wave is called PR interval. It is a measure of the delay between the electrical excitation in the atrium and in the ventricle.

Several disorders of the heart have been studied which prevent the heart from operating normally. One such disorder is from degeneration of the LV conduction system, which blocks the propagation of electric signals through some or all of the fast conducting Purkinje fiber network. Portions of the LV that do not receive exciting signals through the fast conducting Purkinje fiber network can only be excited through muscle tissue conduction, which is slow and in sequential manner. As a result, the contraction of these portions of the LV occurs in stages, rather than synchronously. For example, if the wall N is affected by the conduction disorder, then it contracts later than the wall M which is activated through normal conduction. Such asynchronous contraction of the LV walls degrades the contractility (pumping power) of the LV and reduces the LV+dp/dt (maximum positive derivative of the LV pressure) as well.

Another disorder of the heart is when blood in the LV flows back into the LA, resulting in reduced stroke volume and cardiac output. This disorder is called mitral regurgitation and can be caused by an insufficiency of the mitral valve, a dialated heart chamber, or an abnormal relationship between LV pressure and LA pressure. The amount of the back flow is a complex function of the condition of the mitral valve, the pressure in the LV and in the LA, and the rate of blood flow through the left heart pump.

These disorders may be found separately or in combination in patients. For example, both disorders are found in patients exhibiting congestive heart failure (CHF). Congestive heart failure (CHF) is a disorder of the cardiovascular system. Generally, CHF refers to a cardiovascular condition in which abnormal circulatory congestion exists as a result of heart failure. Circulatory congestion is a state in which there is an increase in blood volume in the heart but a decrease in the stroke volume. Reduced cardiac output can be due to several disorders, including mitral regurgitation (a back flow of blood from the LV to the LA) and intrinsic ventricular conduction disorder (asynchronous contraction of the ventricular muscle cells), which are the two common abnormalities among CHF patients.

Patients having cardiac disorders may receive benefits from cardiac pacing. For example, a pacing system may offer a pacing which improves LV contractility, (positive LV pressure change during systole), or stroke volume (aortic pulse pressure), however, known systems require complicated measurements and fail to provide automatic optimization of these cardiac performance parameters. Furthermore, the measurements are patient-specific and require substantial monitoring and calibration for operation. Therefore, there is a need in the art for a system which may be easily adapted for optimizing various cardiac parameters, including, but not limited to, LV contractility, (peak positive LV pressure change during systole, LV+dp/dt), and cardiac stroke volume (pulse pressure). The system should be easy to program and operate using straightforward patient-specific measurements.

SUMMARY OF THE INVENTION

This patent application describes multiple ways to provide optimized timing for ventricular pacing by determining certain intrinsic electrical or mechanical events in the atria or ventricles that have a predictable timing relationship to the delivery of optimally timed ventricular pacing that maximizes ventricular performance. This relationship allows prediction of an atrio-ventricular delay used in delivery of a ventricular pacing pulse relative to a sensed electrical P-wave of the atrium to establish the optimal pacing timing. Also provided are embodiments for measuring these events and deriving the timing relationship above. Those skilled in the art will understand upon reading the description that other events may be used without departing from the present invention.

In several embodiments, these measurements are used to optimize ventricular contractility as measured by maximum rate of pressure change during systole. In other embodiments, these measurements are used to optimize stroke volume as measured by aortic pulse pressure. In other embodiments, a compromise timing of pacing is available to provide nearly optimal improvements in both peak positive pressure change during systole and aortic pulse pressure. In one embodiment, this pacing is provided by adjusting the atrio-ventricular delay time interval, which is the time interval after a sensed P-wave, to deliver a pacing pulse to achieve the desired cardiac parameter optimization.

This summary of the invention is intended not to limit the claimed subject matter, and the scope of the invention is defined by attached claims and their equivalents.

BRIEF DESCRIPTION OF THE DRAWINGS

FIG. 4A is a graph of left ventricle intrinsic pressure as a function of time as referenced to an intrinsic P-wave event.

FIG. 4B is a graph of left ventricle intrinsic electrogram as a function of time as referenced to an intrinsic P-wave event.

FIG. 4C is a timing diagram showing a marker of an intrinsic P-wave and the marker of a ventricular pacing pulse that is optimally timed for maximum LV contractility as referenced to a paced P-wave event;

DETAILED DESCRIPTION

Figure 1:
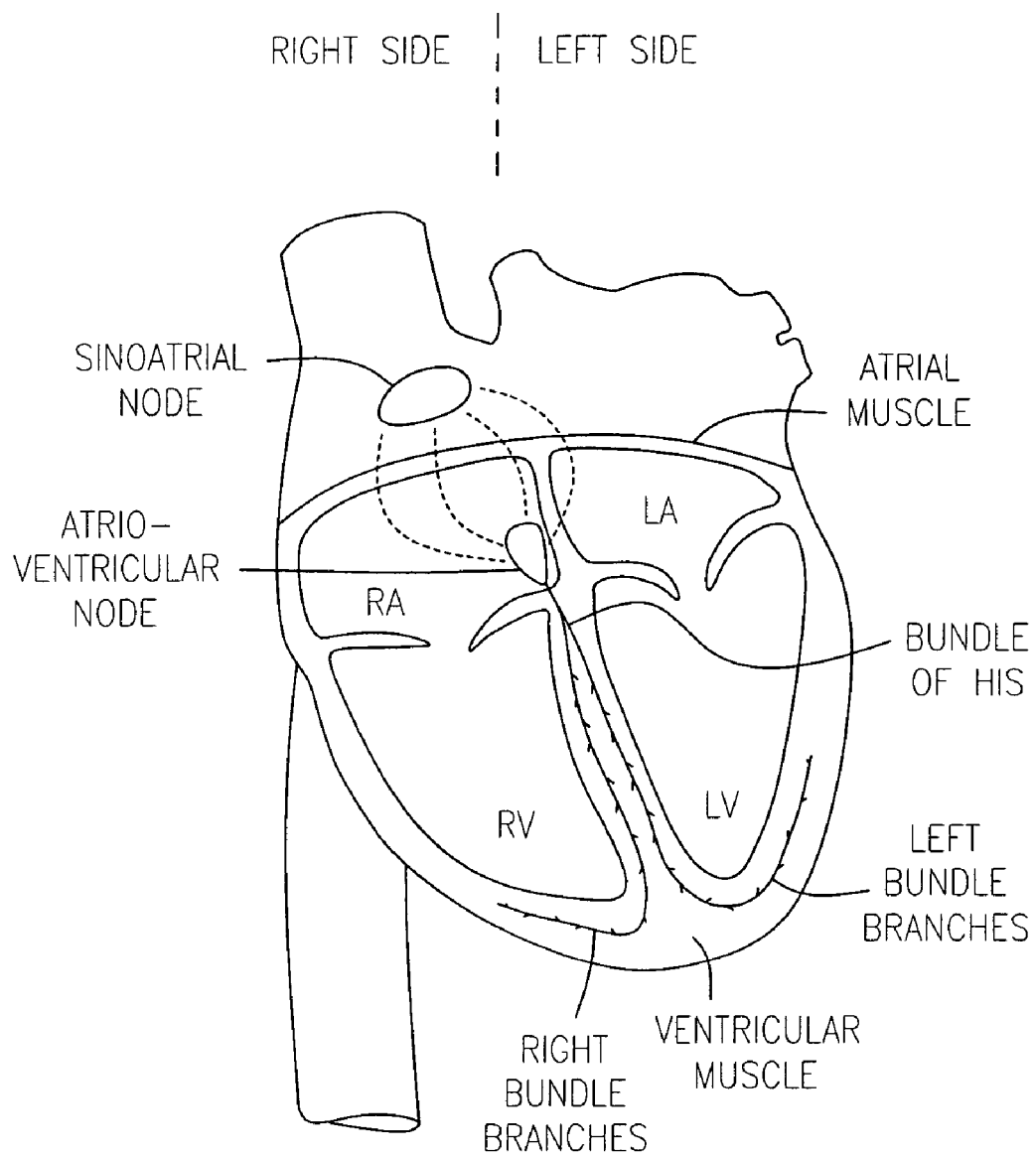
FIG. 1 is a diagram of a heart showing the chambers and the nervous conduction system.
Figure 2:
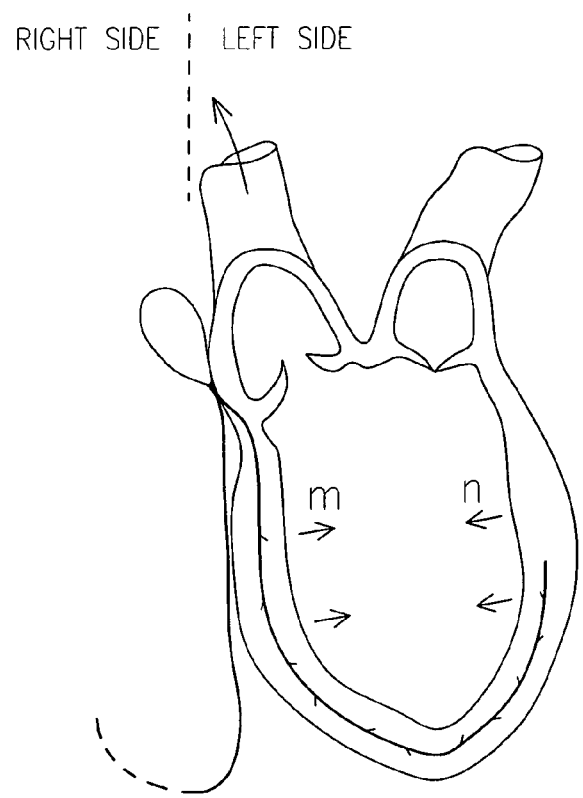
FIG. 2 is a diagram of a ventricle beginning contraction.
Figure 3:
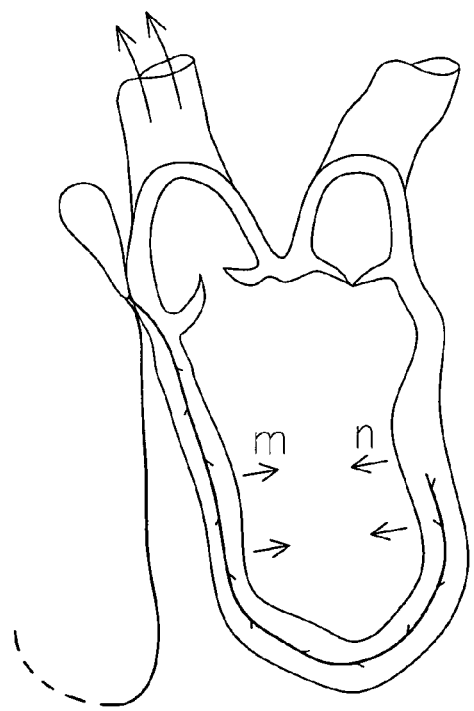
FIG. 3 is a diagram of a contracted ventricle.

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

Some of the embodiments illustrated herein are demonstrated in an implantable cardiac pacemaker, which may include numerous pacing modes known in the art. However, these embodiments are illustrative of some of the applications of the present system, and are not intended in an exhaustive or exclusive sense. For example, the present system is suitable for implementation in a variety of implantable and external devices.

The present system provides a means for optimizing cardiac systolic function based on different cardiac performance measurements. The present disclosure provides a number of embodiments useful for, among other things, optimizing cardiac pumping strength and stroke volume. The concepts described herein may be used in a variety of applications which will be readily appreciated by those skilled in the art upon reading and understanding this description. The cardiac performance measurements expressly provided herein include contractility, peak positive ventricular pressure change, stroke volume, and pulse pressure. Other cardiac performance may be maximized using the teachings provided herein, and therefore, the express teachings of this disclosure are not intended in an exclusive or limiting sense. These concepts are expressly described in terms of the left ventricle, however, applications to other chambers of the heart, including the right ventricle, may be readily appreciated by those skilled in the art without departing from the present invention.

The inventors of this subject matter performed numerous tests and experiments to develop a pacing system which may be used to treat cardiac disorders. The system includes method and apparatus which are useful for providing optimization of different cardiac performance parameters, including, but not limited to, ventricular contractility, maximum rate of pressure change during systole, stroke volume, and pulse pressure. The embodiments provided herein use right atrial (RA) sensing events to time the pacing of the left ventricle (LV), right ventricle (RV), or both (BV) to optimize cardiac performance parameters. However, it is understood that these teachings are applicable to other pacing configurations. The teachings herein provide, among other things, optimal pacing which is selectable for treating different cardiac disorders. The disorders include, but are not limited to, congestive heart failure (CHF), mitral regurgitation, and ventricular conduction disorder. The optimal pacing taught herein includes embodiments which do not use patient-specific measurements of hemodynamic parameters, such as pressure, blood flow, or measurements not typically provided by implantable pacing devices, and the system is capable of automatic adjustment to meet the needs of a particular patient.

AVD Time Intervals

Implantable rhythm management devices such as pacemakers, are useful for treating patients with abnormal cardiac functions. One pacing therapy is called DDD pacing mode. In DDD pacing mode, pacing electrodes are placed in the atrium (for example, the RA) and one or both of the ventricles. These electrodes are also used to sense electric signals from the atrium and the ventricle(s). If the device senses a signal in the atrium, it will inhibit the delivery of a pacing pulse to the atrium, otherwise it will pace the atrium after the end of a predetermined time period. Whenever the device senses or paces the atrium, it generates an event marker and at the same time starts an atrio-ventricular delay (AVD) time interval. At the end of this delay interval, the device will pace the ventricle(s) if no signals from the ventricle(s) are sensed by the device. Systems which provide ventricular pacing signals relative to the P-wave of an electrocardiogram signal refer to atrio-ventricular time delay interval (AVD time interval) as the time delay from the sensed P-wave to the delivery of the ventricular pacing signal. In patients exhibiting ventricular conduction disorder, such as the CHF condition, therapy using an AVD time interval which is shorter than the PR time interval may provide improved contractility because patients with degeneration of their LV conduction system require pacing of the affected parts of the LV (for example, the lateral wall N) early enough so that the contraction may be in phase with other parts of the LV that are excited by intrinsic conduction (for example wall M). Properly timed ventricular pacing can make both walls M and N contract in phase for increased contractility.

Patients with decreased stroke volume benefit from a shorter AVD time interval to decrease the mitral regurgitation effects and increase aortic pulse pressure. In addition, for congestive heart failure (CHF) patients, their PR interval may be prolonged which reduces the AV synchrony to some extent. Such a reduction in AV synchrony may further increase mitral regurgitation, and reduce the effect of preload of the LV. Use of a shorter AVD time interval increases pulse pressure by forcing the contraction of the LV into an earlier period, thus reducing the effects of mitral regurgitation.

Optimization of Cardiac Ventricle Contractility and Maximum Left Ventricle Pressure Change during Systole Left ventricle contractility (pumping power) and peak positive rate of change of left ventricle pressure during systole (abbreviated as "LV+dp/dt") are related cardiac performance parameters. For instance, increases in LV contractility are observed in measurements as increases in left ventricle pressure change during systole.

Figure 4D:
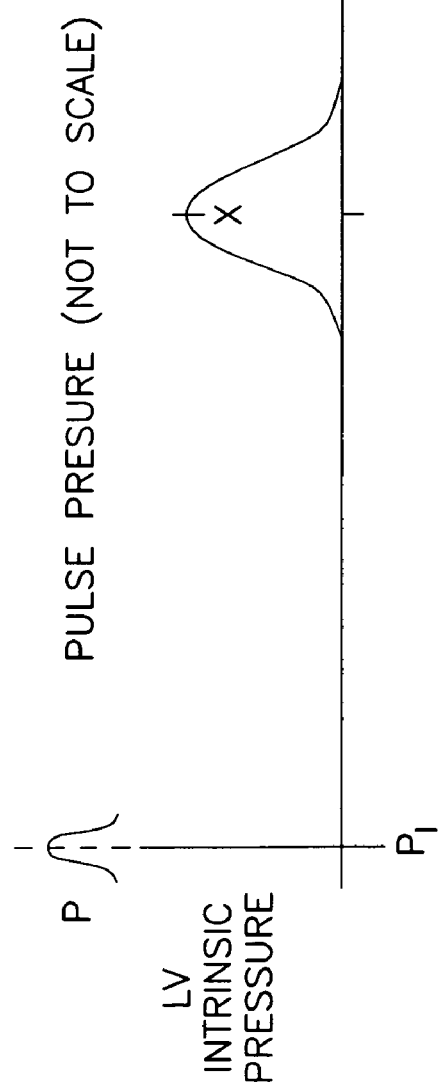
FIG. 4D is a graph of left atrial intrinsic pressure as a function of time as referenced to an intrinsic P-wave event.

FIG. 4A shows an intrinsic or unpaced left ventricle pressure curve following a P-wave. The Y event is the onset of intrinsic LV pressure increase. FIG. 4B shows an intrinsic left ventricular electrogram which is a QRS complex following a P-wave. Q* is an electrical signal which occurs at the beginning of a QRS complex. R is the largest peak of the QRS complex. In FIG. 4B, the Q* event leads the Y event of FIG. 4A. FIG. 4C shows a timing diagram under an optimally paced condition in which the LV contractility is maximized. The $AVD_c$ time interval is equal to the time between the P-wave marker and the ventricular pacing marker V and that pacing provides maximum LV contractility. It is therefore called an optimal atrio-ventricular delay for contractility. It is noted that in the FIG. 4C the $P_p$ marker is from a paced condition, as opposed to the $P_I$ markers in FIGS. 4A and 4B, which arise from intrinsic heart activity. Therefore $P_p$ occurs at a different time than $P_I$. Additionally, the diagrams are not to scale.

Figure 7:
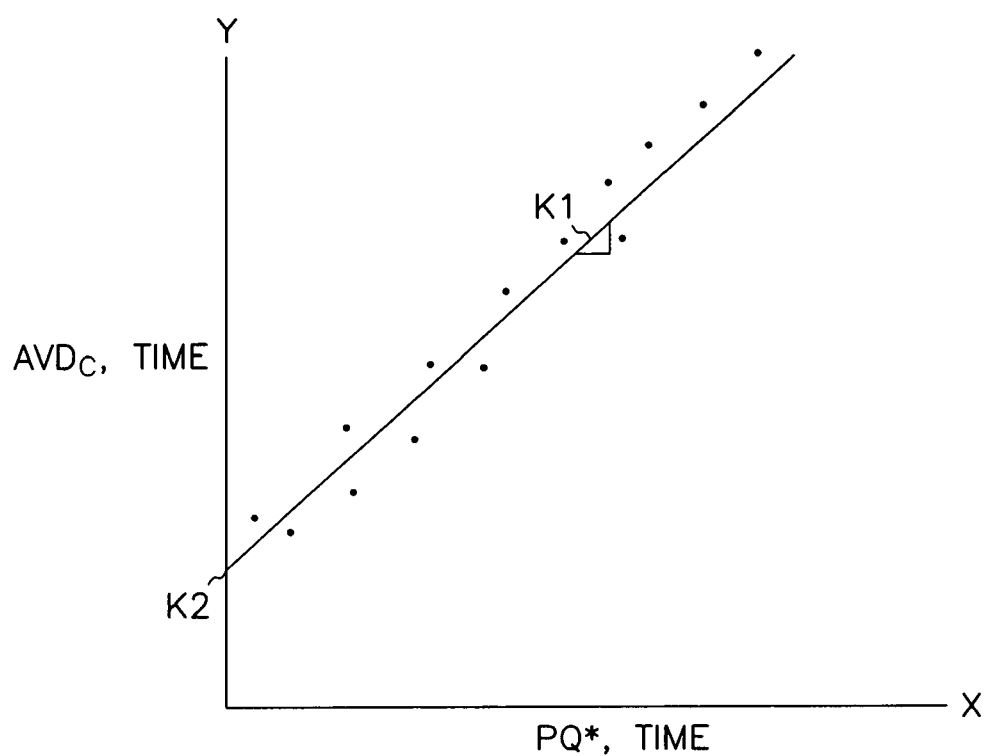
FIG. 7 shows an embodiment of a predetermined mapping according to the present subject matter.

In their experimentation, the inventors learned that when pacing for maximum contractility the Q*, Y, and R events had a relatively predictable timing relationship with respect to the V pacing signal that is optimally timed by $AVD_c$. Furthermore, the inventors learned that linear models could be created which map the PQ* interval (the time difference between a P event and a Q* event) to an optimal atrio-ventricular delay for maximum contractility, $AVD_c$ (FIG. 7 showing one embodiment). Additionally, linear mappings are possible for PY and PR to $AVD_c$, however, each mapping may result in different coefficients.

In one embodiment, an intrinsic PQ* time interval is measured for a patient. This is the time interval between the P-wave and a Q* event when no pacing signal is applied. After the PQ* time interval is recorded and averaged, then a pacing signal is applied with varying atrio-ventricular delays while monitoring LV+dp/dt (peak positive left ventricular pressure change). Then the atrio-ventricular delay which produced the maximum LV+dp/dt (optimal contractility) is determined and named as $AVD_c$, and is paired with that patient's PQ* time interval. The PQ*, $AVD_c$ pairs are generated for a number of other patients and the data are plotted. In one embodiment, a linear regression method is applied to determine a straight line approximation for $AVD_c$ as a function of PQ*. The equation is: AVDC=K1(PQ*)–K2. A programmable device which measures the intrinsic PQ* interval can estimate $AVD_c$ using this equation. Therefore, once K1 and K2 are determined, the calibration of the device is complete. This means that subsequent patients may have optimal contractility pacing without requiring the pressure measurements and additional calibration stages. As described below, the same procedures may be used with PY or PR, however, as stated before, the coefficients may be different.

This means that, if PQ* is measured, then a patient may receive optimal contractility pacing of the left ventricle using measurements of the P-wave and of Q*. In the case where PY is used instead of PQ*, then the measurements will be of the P-wave and of the Y event, which is the onset of pressure increase in the left ventricular contraction. If the PR interval is used, then the measurements will be the P-wave and the R-wave of the QRS complex.

Therefore, given a patient's intrinsic PQ* or PY or PR time interval and the respective mapping, an $AVD_c$ is calculated. This $AVD_c$ is an approximation of the actual $AVD_c$ using the mapping method.

It is noted that any event which is relatively constant with respect to the optimally timed V pacing signal (pacing using $AVD_c$) may be used as a predictable event for use in the present system. In one embodiment, an event which is relatively constant is one which has a deviation between the lesser of 20 ms or 25 percent of the population mean. Therefore, other embodiments incorporating events not expressly mentioned herein may be used without departing from the present system.

P-Wave Signal

When the electronic P-wave signal is used as a reference for any of the embodiments, the P-wave signal is detectable using devices including, but not limited to, catheters or external probes to create electrocardiograms. In one embodiment, the P-wave is sensed from the right atrium and used as a reference for the time interval measurements and pacing delivery. In some cases where a patient's atrium is paced then the P-wave pacing marker is used instead of the intrinsic P-wave.

PQ* Measurement and Mapping

As stated above, the inventors determined some "events" would have a predictable relationship to the optimally timed ventricular pacing signal. The Q* event was defined as one candidate because it is relatively constant relative to the LV pacing mark, V, at optimal timing for maximum contractility. Q* is an electrical signal which occurs at the beginning of a QRS complex. Therefore, in one embodiment of the system, the time delay between the P-wave and the Q* event is used to provide the linear variable to calculate $AVD_c$. In this embodiment, the equation is: $AVD_c$=K1 (PQ*)–K2.

Furthermore, the inventors of the present system realized that the PQ* interval provides a linear variable which may be used to estimate $AVD_c$ using a single calibration procedure for determining the constants K1 and K2. One type of calibration was discussed above, mapping $AVD_c$, PQ* pairs in a linear fashion to provide K1 and K2. The PQ* and $AVD_c$ information is then plotted on a two-dimensional chart and a linear regression method is performed to provide a best line fit through the sample point pairs. This linear fit provides the K1 and K2 coefficients.

In one study using 13 patients, an equation for $AVD_c$ was generated which provided K1 equal to 0.94 and K2 equal to 55.7 milliseconds. In this equation, PQ* is measured in milliseconds. This equation is expressed as: $AVD_c$=0.94 PQ*– 55.7 milliseconds. It is noted that the coefficients may vary and that estimated $AVD_c$ may depart from the actual optimum $AVD_c$ by approximately 20 percent and continue to provide near optimal performance within 80 percent of the maximum contractility. Furthermore, the coefficients may vary slightly depending on the number of samples taken in the calibration stage. Therefore, the coefficients provided herein may vary without departing from the present invention.

Figure 5:
FIG. 5 is a flow diagram for detection of a Q* event.

In one embodiment, the P-wave was detected using a threshold detector which indicated a P-wave at approximately 20 percent of the maximum P-wave amplitude in the right atrium. In one embodiment shown in FIG. 5, the Q* event is determined by passing the QRS complex as sampled from the left ventricle through a 5 point low-pass digital filter having a sampling time of 2 milliseconds, detecting the Q portion of the wave, calculating a maximum absolute value of the slope for the Q-wave, and indicating a point on the filtered Q-wave where the absolute value of the slope equals 2% of the absolute value slope of the Q-wave. Those skilled in the art will readily recognize that other determination methods may be used for P and Q* which do not depart from the present system. Changes in the measurement techniques and slope criteria do not depart from the present system.

In another embodiment, the coefficient of PQ*, K1, is assumed to be unity, and the coefficient K2 amounts to an offset time delay from the PQ* interval to predict or estimate the optimal $AVD_c$. In this embodiment, PQ* and $AVD_c$ are sampled for a variety of patients at a variety of PQ* intervals and a variety of $AVD_c$ to generate a mean offset time delay K2 for a number of patients. In this embodiment, the equation is as follows: $AVD_c$ estimated=PQ*–Wa milliseconds. Using the previous data for the 13 patients, the equation is: $AVD_c$ estimated=PQ*–67 milliseconds. This embodiment provides an easier calculation, since a subtraction is less processor intensive than multiplications using floating point numbers. However, some accuracy is lost for the approximation.

It is noted that the coefficients may vary and that the estimated $AVD_c$ may depart from the actual optimum $AVD_c$ by approximately 20 percent and continue to provide near optimal performance within 80 percent of the maximum contractility. Furthermore, the coefficients may vary slightly depending on the number of samples taken in the calibration stage. Therefore, the coefficients provided herein may vary without departing from the present invention.

Those skilled in the art will readily recognize that other methods may be employed to generate other fits to the data which do not depart from the scope of the present invention.

In one embodiment, the measurements of the P-wave and Q* are provided using an electrode implanted in the right atrium and an electrode implanted in the left ventricle. A programmable pulse generator is used to sense the P-wave and measure the time between occurrence of a sensed P-wave and a sensed Q* event. The Q* event is determined by electronics in the pulse generator which perform the required slope and comparison operations to determine Q*. After a PQ* time interval is determined, the $AVD_c$ is determined using any of the embodiments described herein and their equivalents. Once the $AVD_c$ is determined, it may be used in the next pacing interval to provide an optimized atrio-ventricular delay based on the PQ* time interval.

It is understood that the Q* event may be defined differently and provide substantially the same results with a different set of parameters, K1 and K2. Furthermore, any electrical signal event which bears a predictable relationship to the beginning of intrinsic LV electrogram signals may be used in place of Q*. For example, in one embodiment the beginning of the RV electrogram may be used in place of Q*. Or in another embodiment, the Q* may be measured by surface ECG as the onset of the signal averaged QRS complex. Furthermore, information from more than one lead may be used to more accurately determine Q*.

PR Measurement and Mapping

In another embodiment, the R-wave peak, which is the largest peak of the QRS complex of an intrinsic LV electrogram, is used since it has a predictable relationship to the delivery of optimally timed ventricular pacing for maximum contractility. In particular, the linear time relationship may be derived in terms of the PR interval for optimal atrio-ventricular delay for optimal left ventricular pressure change during systole. In this case, the equation is: $AVD_c$=N1 PR−N2, where $AVD_c$ is for pacing the LV, and PR is the time interval from right atrial sensing marker to the largest peak of the QRS complex of intrinsic LV electrogram. In one embodiment, the N1 and N2 coefficients are determined by mapping the PR time interval to the optimal $AVD_c$ for a number of patients for optimal left ventricular pressure change during systole. In one study using 13 patients, the coefficient N1 is equal to 0.82 and the coefficient N2 is equal to 112 milliseconds. The equation for this calibration is: $AVD_c$=0.82 PR−112 milliseconds. It is noted that the coefficients may vary and that the estimated $AVD_c$ may depart from the actual optimum $AVD_c$ by approximately 20 percent and continue to provide near optimal performance within 80 percent of the maximum contractility. Furthermore, the coefficients may vary slightly depending on the number of samples taken in the calibration stage. Therefore, the coefficients provided herein may vary without departing from the present invention.

In another embodiment, the N1 coefficient is assumed to be unity, and the PR, $AVD_c$ data pairs are averaged to provide a linear dependence with an offset equal to N2. This embodiment provides an easier calculation, since a subtraction is less processor intensive than multiplications using floating point numbers. However, some accuracy is lost for the approximation. For example, using data in the previous study: AVDC=PR−159 milliseconds. In one embodiment, the R-wave signal is measured by detecting the largest peak of the QRS complex of the intrinsic LV electrogram. Therefore, electrical signals are used in this embodiment to provide the PR time interval, and therefore the optimal atrio-ventricular delay for optimal left ventricular pressure change during systole. The coefficients N1 and N2 are provided in an initial calibration stage, which means that subsequent readings using this embodiment generate the optimal $AVD_c$ automatically upon detection of the PR time interval. Furthermore, the N1 and N2 variables may change in value without departing from the teachings provided herein.

Other features of the QRS complex may be used for measurement. As stated above, these events may be used as long as they have a predictable timing relationship to the delivered pacing for optimal contractility. It is noted that the coefficients may vary and that the estimated $AVD_c$ may depart from the actual optimum $AVD_c$ by approximately 20 percent and continue to provide near optimal performance within 80 percent of the maximum contractility. Furthermore, the coefficients may vary slightly depending on the number of samples taken in the calibration stage. Therefore, the coefficients provided herein may vary without departing from the present invention.

PY Measurements and Mappings

In another embodiment, a mechanical event is provided as a reference instead of an electrical event. In one embodiment, the mechanical event, Y is determined as the beginning of intrinsic LV pressure development. This means that a pressure transducer such as a micromonometer can provide instantaneous pressure data in the left ventricle. In this embodiment, the atrio-ventricular delay optimized for maximum left ventricular pressure change during systole is provided as: $AVD_c$=M1 PY−M2. In one embodiment, a micromonometer is placed in the LV to measure left ventricular pressure change during systole. The PY time interval, which is the time interval from right atrial sensing of the P-wave to the beginning of the intrinsic LV pressure development, is mapped to recorded $AVD_c$ values for maximum left ventricular pressure change during systole. This mapping is plotted to perform a linear regression in order to determine the coefficients M1 and M2. In one study, M1 is equal to 0.96 and M2 is equal to 139 milliseconds. Therefore, in this study, the $AVD_c$=0.96 PY−139 milliseconds. It is noted that the coefficients may vary and that the estimated $AVD_c$ may depart from the actual optimum $AVD_c$ by approximately 20 percent and continue to provide near optimal performance within 80 percent of the maximum contractility. Furthermore, the coefficients may vary slightly depending on the number of samples taken in the calibration stage. Therefore, the coefficients provided herein may vary without departing from the present invention.

In another embodiment, the M1 coefficient is approximated as unity, and then the PY and $AVD_c$ pairs are used to determine a linearized mapping which amounts to: $AVD_c$=PY−$N_a$, where $N_a$ is an averaged offset delay for the samples taken. In one embodiment, $AVD_c$=PY−150 milliseconds. This embodiment provides an easier calculation, since a subtraction is less processor intensive than multiplications using floating point numbers. However, some accuracy is lost for the approximation. Again, it is noted that the coefficients may vary and that the estimated $AVD_c$ may depart from the actual optimum $AVD_c$ by approximately 20 percent and continue to provide near optimal performance within 80 percent of the maximum contractility. Furthermore, the coefficients may vary slightly depending on the number of samples taken in the calibration stage. Therefore, the coefficients provided herein may vary without departing from the present invention.

Figure 6:
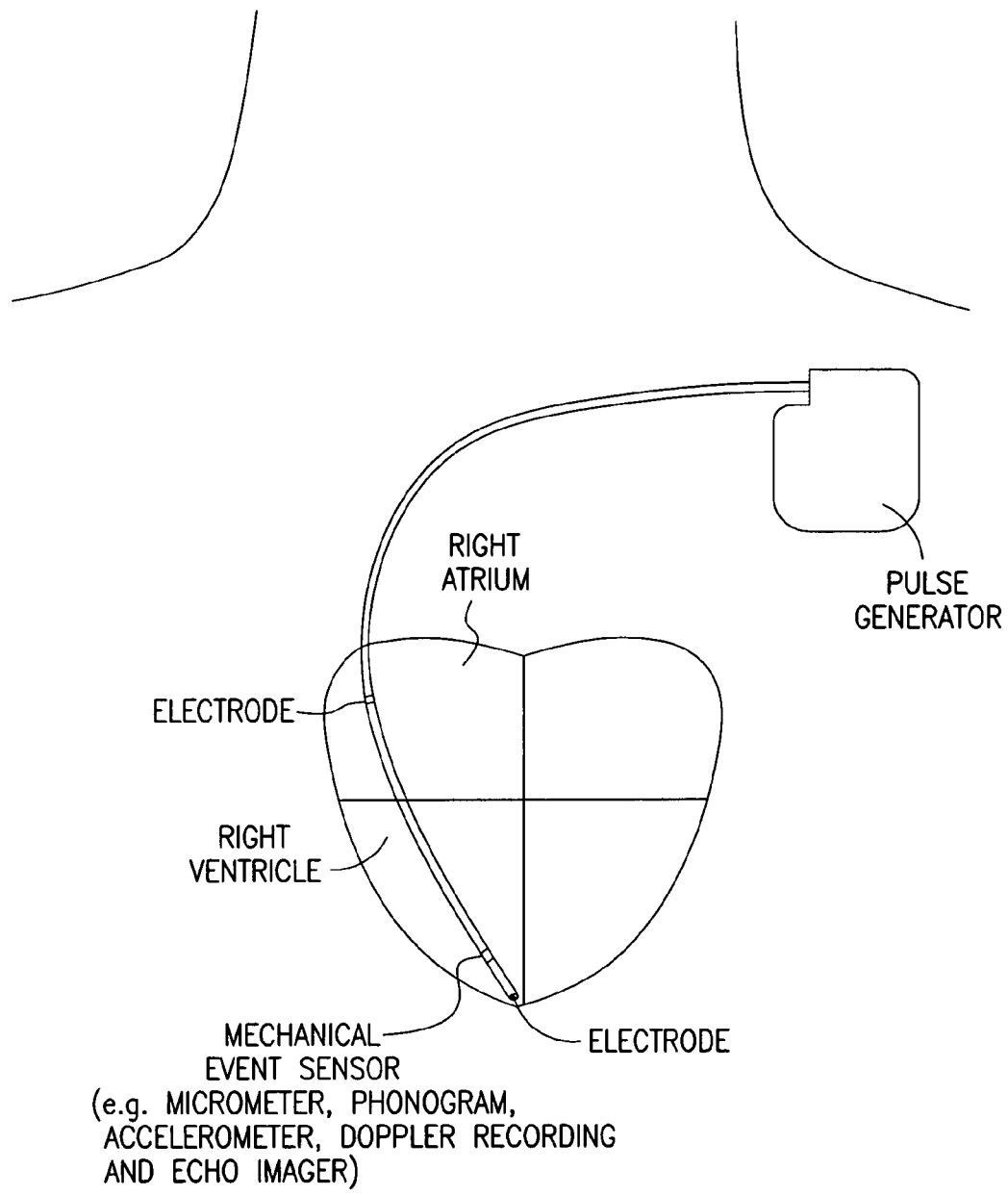
FIG. 6 shows embodiments of the apparatus for the present subject matter.

Other mechanical events may be used as long as they are relatively predictable with respect to the Y event. The Y events may be selected from signals including, but not limited to, ventricular pressure, cardiac phonogram, cardiac acoustic signals (such as recorded from an accelerometer external to or inside an implantable device), Doppler recording of atrio-ventricular valve motion, and M-mode, 2D, or 3D echo imaging of ventricular wall motion (FIG. 6 showing one embodiment of the mechanical event sensor).

Stroke Volume Optimization Using Atrio-Ventricular Delay

Figure 4E:
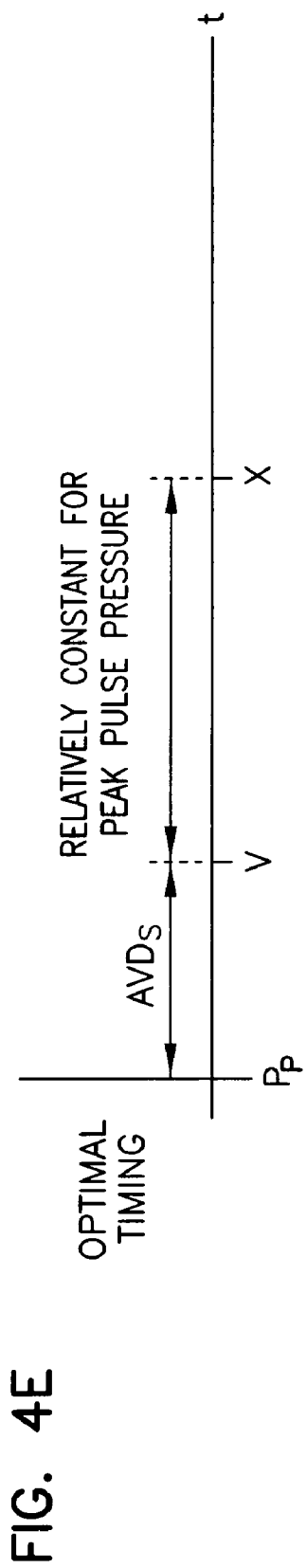
FIG. 4E is a timing diagram showing a marker of an intrinsic P-wave and the marker of a ventricular pacing pulse that is optimally timed for maximum stroke volume as referenced to a paced P-wave event.

Stroke volume is related to pulse pressure. The inventors discovered that for maximum pulse pressure (stroke volume), there is a predictable timing relationship between an optimally delivered ventricular pulse V and the peak of left atrial systole, X. Therefore, the optimal atrio-ventricular delay for maximum pulse pressure, $AVD_s$, is determined by PX time interval measurements, as shown in FIG. 4E.

In one embodiment, stroke volume is optimized by determining the atrio-ventricular delay for maximum aortic pulse pressure, $AVD_s$. In one embodiment, the X event is measured by placing a pressure sensing catheter inside the LA. In another embodiment, the X event is detected by measuring the LV pressure, because the LA contraction is seen in the LV pressure curve by a pre-systolic component. The peak of the LA systole is considered the same as the pre-systolic pressure in the LV pressure curve. The time interval between P and the pre-systolic component of LV pressure provides a linear equation. Therefore, in order to generate the linear mapping of PX to $AVD_s$, a number of PX, $AVD_s$ pairs are generated by measuring maximum aortic pulse pressure for varying PX. The linear relationship is expressed by: $AVD_s=M3\ PX-M4$ milliseconds. In one embodiment, a calibration procedure was performed to generate a number of PX, $AVD_s$ pairs, which are mapped and a best line fit is performed to determine M3 and M4. In one embodiment, M1 is equal to 1.22 and M2 is equal to 132 milliseconds. Therefore, the $AVD_s$ relationship is: $AVD_s=1.22\ PX-132$ milliseconds. It is noted that the coefficients may vary and that the estimated $AVD_s$ may depart from the actual optimum $AVD_s$ by approximately 20 percent and continue to provide near optimal performance of the maximum stroke volume. Furthermore, the coefficients may vary slightly depending on the number of samples taken in the calibration stage. Therefore, the coefficients provided herein may vary without departing from the present invention.

In one embodiment, the P-wave event is measured using a threshold detection where the P-wave is determined to be 20% of the maximum P-wave amplitude. Other detection methods for the P-wave may be used without departing from the present system. The X event may be determined by several ways, including but not limited to: locating the point of maximum atrial pressure, Doppler measurements, and S4 components of accelerator measurements.

Other embodiments using different values for M3 and M4 are possible without departing from the present system. Furthermore, other markers may be used which are directly related to the PX time interval provided in one embodiment.

It is noted that any event which is relatively constant with respect to the optimally timed V pacing signal (pacing using $AVD_s$) may be used as a predictable event for use in the present system. In one embodiment, an event which is relatively constant is one which has a deviation between the lesser of 20 ms or 25 percent of the population mean. Therefore, other embodiments incorporating events not expressly mentioned herein may be used without departing from the present system.

Selection of Atrio-Ventricular Delay for Improved Contractility and Stroke Volume Depending on the condition of a heart and its disorders, optimal atrio-ventricular delay for maximum contractility may provide especially nonoptimal stroke volume. Likewise, optimal atrio-ventricular delay for maximized stroke volume may result in nonoptimal contractility. Therefore, in order to provide a compromised atrio-ventricular delay which provides an approximately optimal atrio-ventricular delay for both contractility and stroke volume, $AVD_{cs}$, it is desirable to have an atrio-ventricular delay which provides near optimal contractility and near optimal stroke volume. The inventors of the present system derived a relationship which provides a compromise between optimal contractility and optimal stroke volume. In one embodiment, the optimized atrio-ventricular delay, $AVD_{cs}$, is a linear relationship in the PR time interval, as follows: $AVD_{cs}=K3\ PR_m-K4$ milliseconds. $PR_m$ is a time interval measured from a right atrial sensing marker, P, to a right ventricular sensing marker, $R_m$. In one embodiment, the compromised $AVD_{cs}$ is provided by determining $AVD_c$ and $AVD_s$ for a number of PR values and for a number of patients. Then a linear regression provides a best line fit for both contractility and stroke volume. In one embodiment, $AVD_{cs}$ equals $0.5\ PR_m-15$ milliseconds, where $AVD_{cs}$ is for pacing at least one ventricle, and where the time interval $PR_m$ is measured from a right atrial sensing marker, P, to a right ventricular sensing marker, $R_m$. In this embodiment, the resulting atrio-ventricular delay provides a left ventricular pressure change within 90% of the optimal left ventricular pressure change during systole. Furthermore, this embodiment provides an aortic pulse pressure which is within 80% of the optimal aortic pulse pressure. It is noted that the coefficients may vary and still provide a reasonable approximation of $AVD_{cs}$. For example, in one embodiment K3 may be in the range from 0.4 to 0.6 and K2 may be in the range from 0 to 30 ms. Therefore, the present system offers flexibility in the selection of coefficients, and those provided are demonstrative and not an exclusive set of coefficients.

In one embodiment, a left ventricular event is used to provide a time interval for calculation of $AVD_{cs}$. In one case the LV event is the LV R-wave. The LV R-wave marker signal may also be used as an event. It is noted that any event which is relatively constant with respect to the near optimally timed V pacing signal may be used as a predictable event for use in the present system. In one embodiment, an event which is relatively constant is one which has a deviation between the lesser of 20 ms or 25 percent of the population mean. Therefore, other embodiments incorporating events not expressly mentioned herein may be used without departing from the present system.

In one embodiment, the left ventricular R wave is used to develop a relationship between the PR interval (the time interval between a P event and an R event) and $AVD_{cs}$. For a particular patient, the intrinsic PR interval is measured. Additionally, a sweep of atrio-ventricular delays are applied to the pacing of the patient and LV+dp/dt and pulse pressure are measured for each different atrio-ventricular delay. The LV+dp/dt data is plotted against a normalized value of the atrio-ventricular delay. Additionally, the pulse pressure is also plotted against a normalized value of the atrio-ventricular delay. In one embodiment, the atrio-ventricular delay is divided by PR−30 ms to normalize the delay. The tests are performed for a number of additional patients and the normalized plots are mapped. Then an averaging of the various LV+dp/dt vs. normalized atrio-ventricular delay data is performed. An averaging of the pulse pressure data vs. normalized atrio-ventricular delay data is also performed. The atrio-ventricular delay (normalized value) at the LV+dp/dt curve peak is used as an optimal averaged atrio-ventricular delay. The peak of the pulse pressure curve is also determined. In one example, the optimal averaged normalized atrio-ventricular delays for both curves was determined to be approximately 0.50 times the normalized PR time interval, or 0.50 (PR−30) milliseconds.

In one study data was taken using a series of intermittent pacing (5 pacing beats in every 15 sinus beats) from one of three sites (RV, LV, and BV) at one of five AV delays (equally spaced between 0 msec and PR−30 msec). Each pacing site/ AV delay combination was repeated five times in random order. Pressure and electrogram data were recorded from the ventricles. LV+dp/dt and PP were measured from LV and aortic pressure recordings on a beat-by-beat basis. For each paced beat, values of the LV+dp/dt and PP were compared to a preceding 6-beats-averaged sinus baseline. Then the response to pacing configuration was averaged. However, other measurements may be taken to obtain the required information.

Switchable Pacing Therapies

Any of the teachings provided herein may be employed in a variety of cardiac devices, including implantable pacing devices. In one embodiment, an implantable device also includes means for changing the ventricular pacing to adjust for maximum contractility, maximum stroke volume or a compromise providing nearly optimal contractility and stroke volume. In such an embodiment, the pacing system contemplates the use of all of the different optimal atrio-ventricular delays to adjust the therapy to a cardiac patient. In one embodiment $AVD_{cs}$ is used as a default atrio-ventricular pacing delay, which may be maintained or modified at a later time depending on the therapy required. For example, in one embodiment of the system, the pacing initiates with an atrio-ventricular delay equal to $AVD_{cs}$. If at any time an optimal contractility is required, the atrio-ventricular pace delay is changed to $AVD_c$. Additionally, if at any time optimal stroke volume is required, the atrio-ventricular delay is changed to $AVD_s$. Other variations and combinations are possible without departing from the present invention. Furthermore, the switching of the pacing therapies may be provided by an external instruction, such as a programmer, or by an internally executing software for selecting the appropriate therapy. Other ways of switching between therapies may be encountered which do not depart from the present system.

CONCLUSION

The present pacing system may be employed in a variety of pacing devices, including implantable pacing devices. The present system may be used for pacing one or more ventricles. A variety of pacing electrode configurations may be employed without departing from the present invention including multiple pacing sites at a ventricle(s), provided that the required electrical or mechanical events are monitored. Changes in the coefficients and order of methods provided herein may be practiced accordingly without departing from the scope of the present invention.

What is claimed is:

1. A method, comprising:
    monitoring a signal representing ventricular electrical activity;
    detecting an intrinsic ventricular electrical event;
    measuring a time interval between an atrial event and the intrinsic ventricular electrical event;
    calculating an AVD using the time interval and a predetermined mapping of a relationship between the time interval and an approximately optimal atrial-ventricular delay (AVD) associated with ventricular pacing that maximizes peak positive left ventricular pressure change; and
    delivering a pacing pulse using the calculated AVD.

2. The method of claim 1, wherein monitoring the signal representing ventricular electrical activity comprises recording an electrogram endocardially or epicardially from a ventricle.

3. The method of claim 2, wherein recording the electrogram comprises recording a left ventricular electrogram.

4. The method of claim 3, wherein detecting the intrinsic ventricular electrical event comprises detecting an R-wave.

5. The method of claim 3, wherein detecting the intrinsic ventricular electrical event comprises detecting a beginning of a QRS complex, Q*.

6. The method of claim 1, wherein monitoring the signal representing ventricular electrical activity comprises monitoring a surface ECG.

7. The method of claim 6, wherein detecting the intrinsic ventricular electrical event comprises detecting an onset of a signal averaged QRS complex, Q*.

8. The method of claim 1, wherein detecting the intrinsic ventricular electrical event comprises detecting a beginning of a QRS complex, Q*.

9. The method of claim 8, wherein detecting Q* comprises detecting Q* using a plurality of electrograms.

10. The method of claim 8, wherein detecting Q* comprises:
    filtering the signal representing ventricular electrical activity to provide a filtered signal;
    detecting a portion of the filtered signal related to a Q-point; and
    finding the beginning of the QRS complex, Q*, at a position where a slope of the filtered signal related to the Q-point is a predetermined ratio of the maximum slope of the filtered signal related to the Q-point.

11. The method of claim 10, wherein finding Q* comprises finding Q* at a position where the slope of the filtered signal related to the Q-point is two percent of the maximum slope of the filtered signal related to the Q-point.

12. The method of claim 1, wherein detecting the intrinsic ventricular electrical event comprises detecting a marker signal delivered by an external or implantable device.

13. The method of claim 12, wherein detecting the marker signal comprises detecting a right ventricular R-wave marker.

14. The method of claim 12, wherein detecting the marker signal comprises detecting a left ventricular R-wave marker.

15. The method of claim 1, wherein measuring the time interval between the atrial event and the intrinsic ventricular electrical event comprises:
    sensing a signal representing atrial electrical activity; and
    detecting an atrial electrical event using the signal representing atrial electrical activity.

16. The method of claim 15, wherein monitoring the signal representing ventricular electrical activity comprises sensing a ventricular electrogram, detecting the intrinsic ventricular electrical event comprises detecting an R-wave, sensing the signal representing atrial electrical activity comprises sensing an atrial electrogram, detecting the atrial electrical event comprises detecting a P-wave, and delivering the pacing pulse using the timing of the atrial electrical event and the timing of the intrinsic ventricular electrical event comprises using a time interval between the P-wave and the R-wave.

17. The method of claim 16, wherein detecting the P-wave comprises detecting an intrinsic P-wave.

18. The method of claim 16, wherein detecting the P-wave comprises detecting a P-wave pacing marker.

19. The method of claim 16, wherein sensing the ventricular electrogram comprises sensing a left ventricular electrogram.

20. The method of claim 16, wherein sensing the ventricular electrogram comprises sensing a right ventricular electrogram.

* * * * *